(12) United States Patent
Anderson

(10) Patent No.: US 7,972,348 B1
(45) Date of Patent: Jul. 5, 2011

(54) SINGLE USE SCLERAL MARKER

(75) Inventor: Nicholas G. Anderson, Knoxville, TN (US)

(73) Assignee: DeRoyal Industries, Inc., Powell, TN (US)

( * ) Notice: Subject to any disclaimer, the term of this patent is extended or adjusted under 35 U.S.C. 154(b) by 303 days.

(21) Appl. No.: 12/401,809

(22) Filed: Mar. 11, 2009

(51) Int. Cl.
*A61F 9/007* (2006.01)

(52) U.S. Cl. .................................................... 606/166

(58) Field of Classification Search ............... 606/79, 606/166, 167, 172, 185, 186; 30/279.2, 280, 30/284–287, 294, 299, 314, 322, 323
See application file for complete search history.

(56) References Cited

U.S. PATENT DOCUMENTS

| | | | | |
|---|---|---|---|---|
| 1,162,669 | A * | 11/1915 | Vinnedge | 606/172 |
| 2,348,429 | A * | 5/1944 | Walker | 30/90.7 |
| 5,165,387 | A | 11/1992 | Woodson | |
| D352,002 | S * | 11/1994 | Culter et al. | D9/435 |
| 5,431,292 | A * | 7/1995 | Culter et al. | 215/48 |
| 5,547,468 | A * | 8/1996 | Simon et al. | 604/21 |
| 5,573,529 | A | 11/1996 | Haak et al. | |
| 5,597,381 | A * | 1/1997 | Rizzo, III | 623/6.63 |
| 5,713,381 | A | 2/1998 | Sloane | |
| 5,713,915 | A * | 2/1998 | Van Heugten et al. | 606/167 |
| 6,113,606 | A * | 9/2000 | Dykes | 606/107 |
| 6,383,133 | B1 | 5/2002 | Jones | |
| 6,422,866 | B2 * | 7/2002 | Dragan et al. | 433/90 |
| 6,440,065 | B1 | 8/2002 | Hered | |
| 6,447,528 | B2 * | 9/2002 | Paraschac | 606/190 |
| 6,516,521 | B1 * | 2/2003 | Rush et al. | 30/294 |
| 6,675,805 | B1 | 1/2004 | Graether | |
| 6,719,771 | B1 * | 4/2004 | Crossman | 606/181 |
| 7,011,003 | B1 * | 3/2006 | Berke | 83/13 |
| 2004/0039399 | A1 | 2/2004 | Norrby et al. | |
| 2004/0200754 | A1 | 10/2004 | Hagemeier | |
| 2005/0226814 | A1 | 10/2005 | Levy | |
| 2007/0038234 | A1 * | 2/2007 | Yaldo | 606/166 |
| 2007/0239183 | A1 * | 10/2007 | Melki | 606/166 |
| 2009/0043322 | A1 * | 2/2009 | Melki | 606/166 |

* cited by examiner

*Primary Examiner* — Ryan J Severson

(74) *Attorney, Agent, or Firm* — Luedeka, Neely & Graham, PC

(57) ABSTRACT

A single-use scleral marker, including a one-piece molded-plastic marker having an elongate body; a pair of opposite forked ends, and a pair of removable guards, each of the guards encircling one of the ends and having connection ends which connect the guard to the body, wherein the connection ends may be broken by exerting a bending force thereon to enable the guard to be removed.

3 Claims, 5 Drawing Sheets

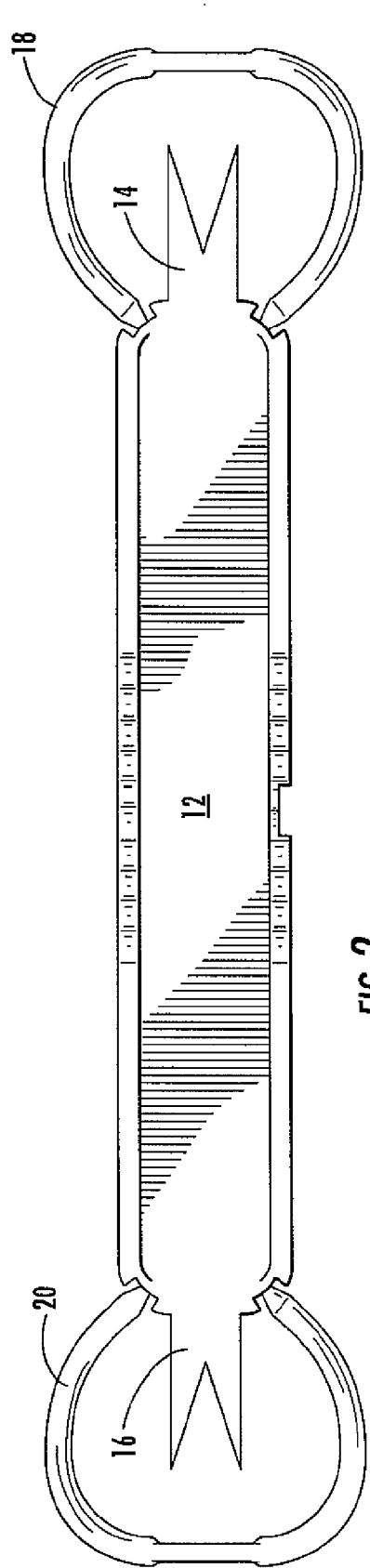
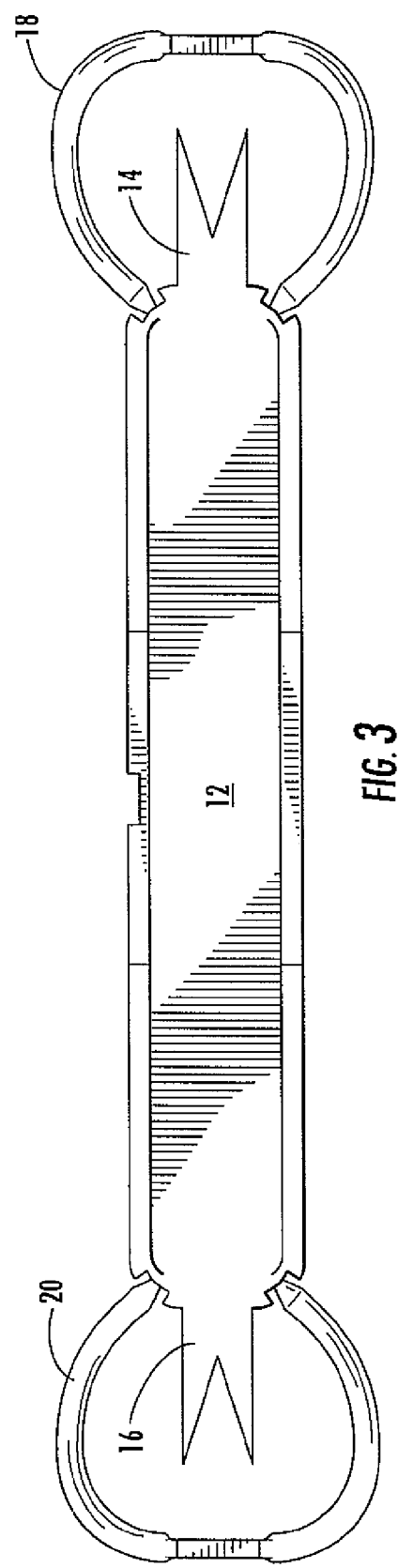
FIG. 2
FIG. 3

SINGLE USE SCLERAL MARKER

FIELD

The present disclosure relates to single use sterile surgical instruments for eye surgery. More particularly, the disclosure relates to single use scleral markers for use in intravitreal injection procedures.

BACKGROUND

Current indications for ophtalmalic intravitreal injections may include: diabetic retinopathy; macular degeneration; ocular infection; retinal swelling; retinal vascular disease, and choroidal neovascular membrane. Intravitreal injection may provide a route of administration of a drug, such as an anesthetic, to the posterior segment of the eye where the drug may reach the retina and sub retinal tissues in higher concentrations than topical or systemic administration may provide.

The injection may be a pars plana injection into the vitreous cavity (intravitreal). The pars plana refers to an internal structure of the eyewall between ciliary body and the retina. It is particularly desirable not to inject through the retina, as this may put a hole in the retina, possibly leading to a retinal detachment. However, if the injection site is too close to the limbus damage to the lens of the eye by the needle may be likely to occur. Therefore, it is desirable that the injection penetrate the pars plana. Since the pars plana may not be directly visualized during the injection, it is desirable that a visible mark be made on the sclera (white part of the eye) prior to the injection. The mark may indicate the location of the underlying pars plana.

Use of a scleral marker is desirable for intravitreal injection because there may be a very narrow range for the injection site. The scleral marker may be used to measure a very precise distance and mark it on the sclera where it may be visible to the physician. Scleral markers typically have a pair of opposite ends, with each end forked to define two points a desired distance depending upon the intended usage. For use in procedures involving adult human eyes, one end has points spaced 3.5 mm apart and the other end has points spaced 4 mm apart. The physician selects which spacing is appropriate for a given patent and procedure. The desired spacings will typically be different for other applications, such as pediatric or for veterinary uses. Thus, specific spacing markers are produced for a given area of practice.

During use of a scleral marker by a surgeon in marking the eye for injection, one point of the marker may be placed at the limbus of the eye and the other point may be pressed in to the sclera of the eye, making an indentation to mark the injection site. Alternatively, a sterile marking pen may be used to apply ink to one of the marker points which may then be transferred to the sclera when the point is placed against the eye wall. Some physicians may make an indentation with the caliper and then highlight that indentation with the sterile marker.

Autoclave or radiation sterilization may typically be employed to sterilize a re-usable marker. Most physicians may perform multiple (>30) injections per day. The sterilization process takes too long to efficiently re-sterilize the instruments between patients. Therefore, multiple, costly, re-usable markers may be purchased to use throughout the day and then sterilized together at the end of the day. Most intravitreal injections are performed outside the operating room in a physician's office. Many offices do not have access to sterilization machinery and therefore the used markers may have to be sent out for sterilization before re-use. If the office does have sterilization equipment, a great deal of staff time may be required for sterilization.

For this reason, disposable or single use plastic scleral markers have become increasingly popular. Typically, a sterile marker is provided in sealed sterilized packaging alone or in combination with other surgical instruments for a procedure, such as a speculum. However, it has been observed that the fine points of the scleral marker may become damaged in the packaging or else penetrate the packaging and compromise the sterile conditions. The disclosure relates to a single use scleral marker configured to protect the points to overcome the disadvantages of conventional single use scleral markers.

SUMMARY OF DISCLOSURE

The disclosure relates to a single-use scleral marker. The marker includes a one-piece molded-plastic marker having an elongate body; a pair of opposite forked ends, and a pair of removable guards.

Each of the guards encircles one of the ends and includes connection ends which connect the guard to the body. The connection ends may be broken by exerting a bending force thereon to enable the guard to be removed.

The markers are economical and represent a useful improvement. The construction cleverly provides a single-use scleral marker having a configuration which protects the points, yet renders the marker easy to configure for use.

In this regard, the disclosure also provides a method of administering a sterile intravitreal injection using a single-use scleral marker. In accordance with the method, a one-piece molded-plastic scleral marker is provided which has an elongate body; a pair of opposite forked ends, and a pair of removable guards. Each of the guards encircles one of the ends and includes connection ends which connect the guard to the body. The connection ends of one of the guards are broken by exerting a bending force, and the guard is removed from one of the forked ends to expose the forked end. The exposed forked end is then used to mark an intravitreal injection site.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein:

FIGS. 2 and 3 are top and bottom plan views, respectively, of a scleral marker according to a preferred embodiment of the disclosure

DETAILED DESCRIPTION

Figure 1:
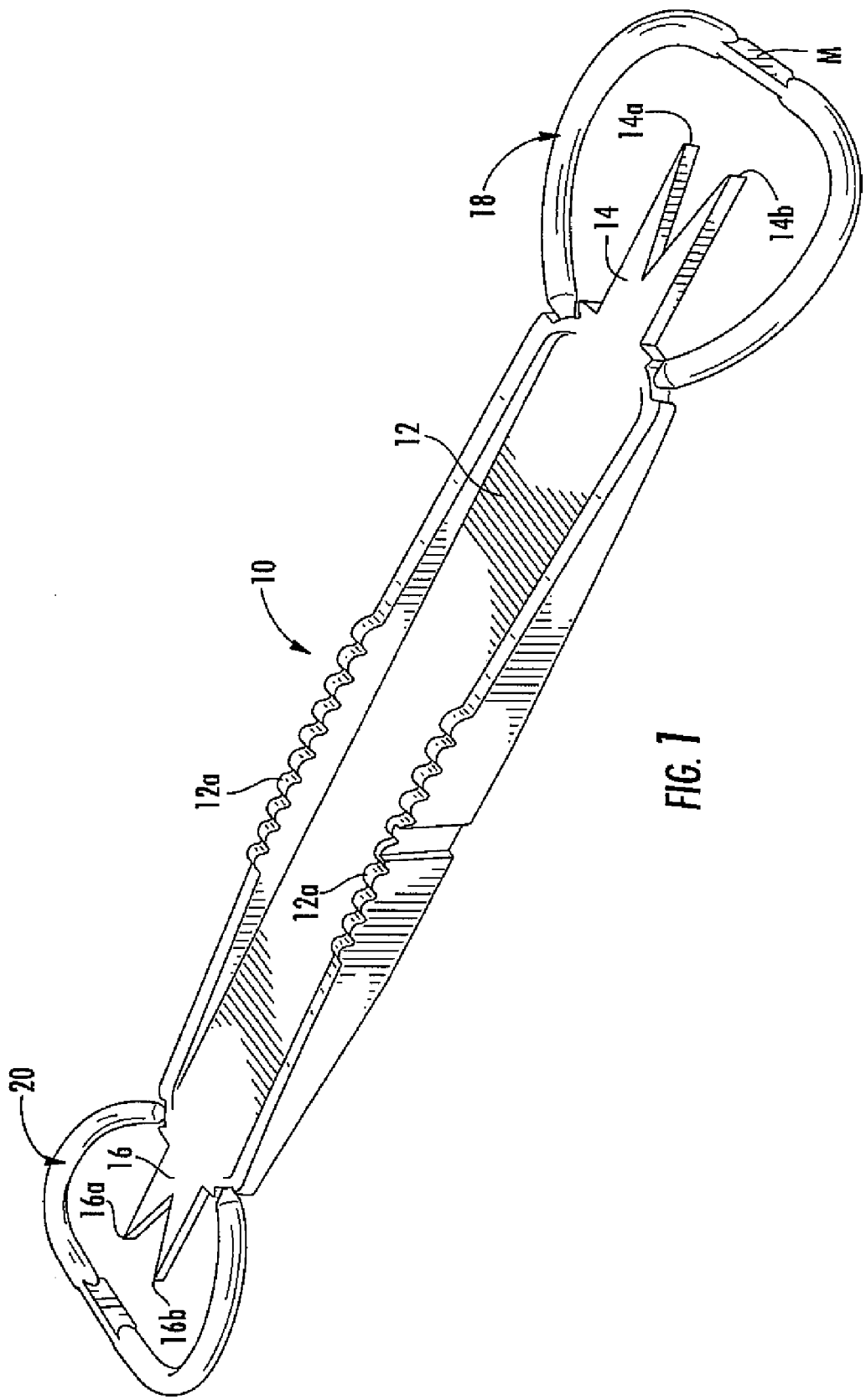
FIG. 1 is a perspective view of a scleral marker.

The disclosure relates to a single use scleral marker 10. The marker 10 is of one-piece molded plastic construction, preferably injection molded, and includes an elongate body 12, a pair of opposite forked ends 14 and 16, and removable guards 18 and 20 which protect the ends 14 and 16.

The body 12 is an elongate, generally flat rectangular shaped member, preferably including serrated edges 12a for facilitating grasping during use. For the purpose of example, the body 12 has a length of about 6 cm, and the overall length of the marker 10 with both of the guards 18 and 20 in place is 9 cm. Each of the ends 14 and 16 extends outwardly a distance of about 1.0 cm from the body 12. The guards 16 and 18 each extend about 1.5 cm beyond the body 12, such that the distance from the points of each forked end to the guard is about 0.5 cm. The width of the body 12 is about 1 cm. The greatest width of the guards 18 and 20 is about 2 cm.

The end 14 is configured to define two points 14a and 14b and the end 16 is configured to define points 16a and 16b, each of the points of an end being spaced apart a desired distance depending upon the intended usage. For use in procedures involving adult human eyes, the points 14a and 14h are preferably laterally spaced 3.5 mm apart and the points 16a and 16b are spaced 4 mm apart. Indicia corresponding to the spacing of the points is preferably included adjacent each end. In this regard, a preferred plastic material for making the marker 10 is polycarbonate, but any polymer having sufficient rigidity to maintain an accurate gap between the points of the forked ends may be utilized.

To protect the points 14a and 14b, the end 14 includes the guard 18 which encircles the points 14a and 14b and lies in a common horizontal plane with the points 14a and 14b. The guard 20 likewise encircles the points 16a and 16b and lies in a common horizontal plane.

The guard 18 is provided as by a molded curved strip 22 having opposite connection ends 22a and 22b each connected to opposite sides of the end 14 adjacent the proximal end of one of the points 14a and 14b. The guard 20 located at the end 16 is substantially identical to the guard 18, and is provided by a molded curved strip 24 having opposite connection ends 24a and 24b.

Figure 4:
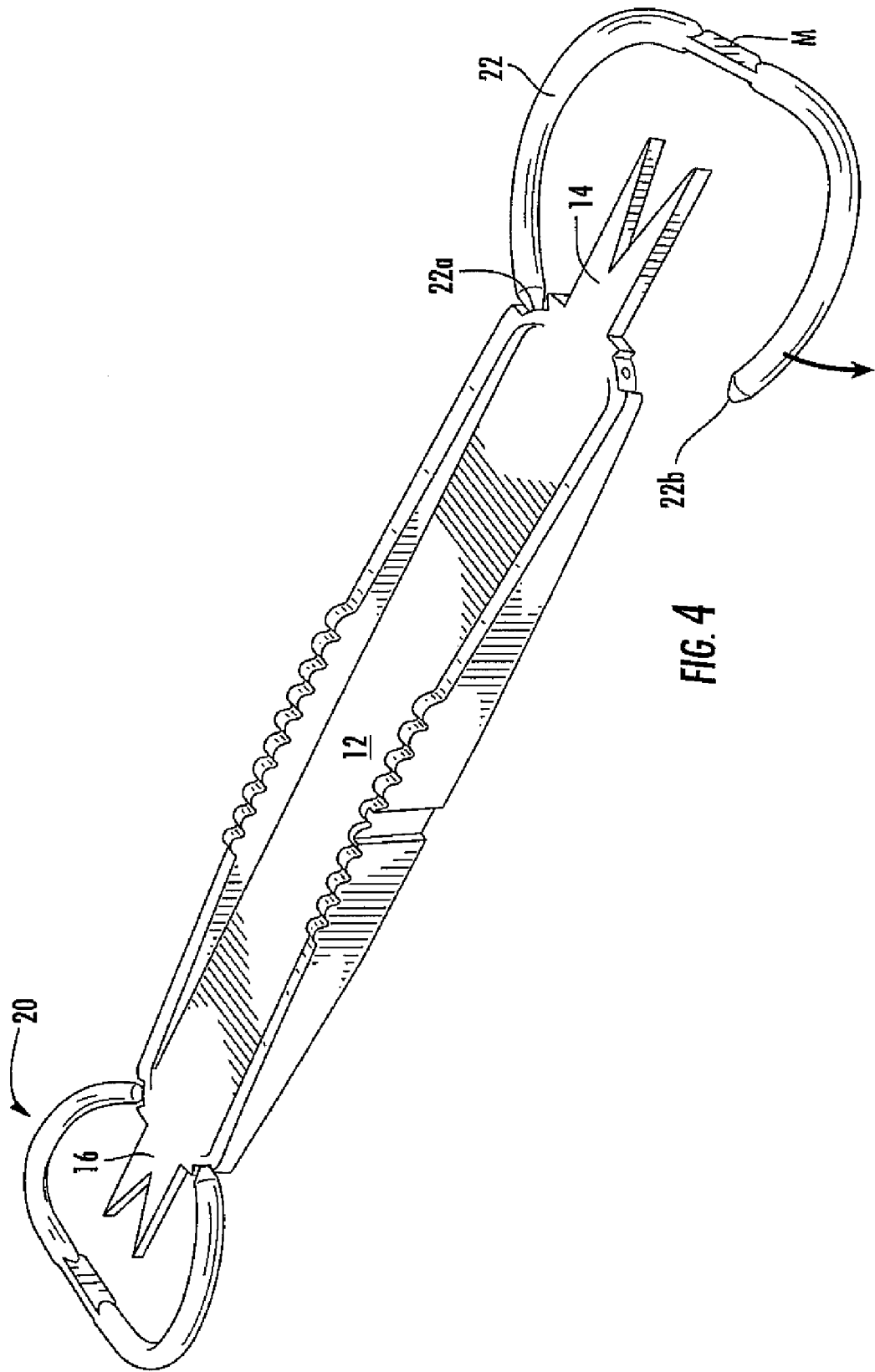
FIGS. 4-5 show removal of a protective guard from the scleral marker.
Figure 5:
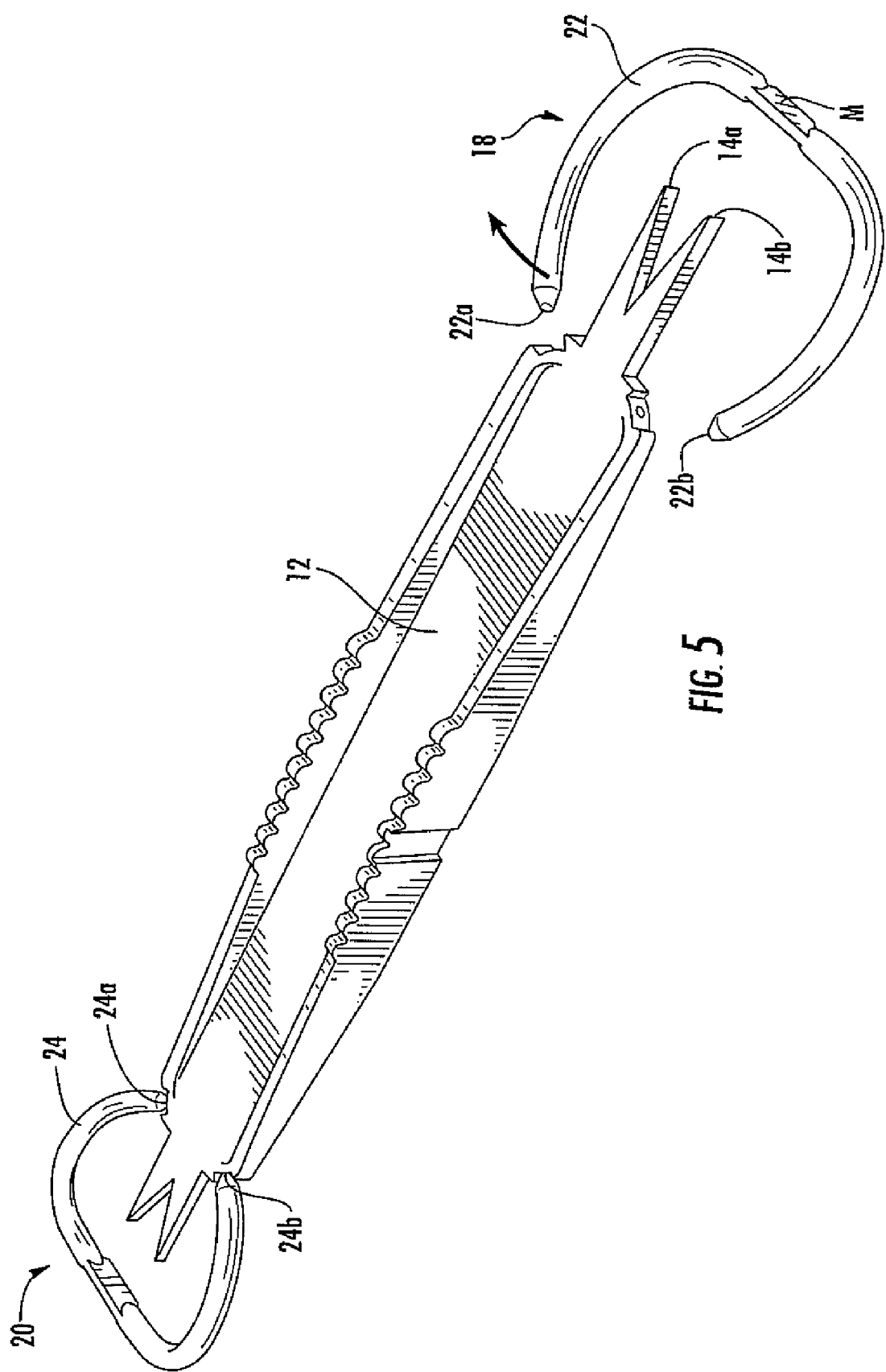
Figure 6:
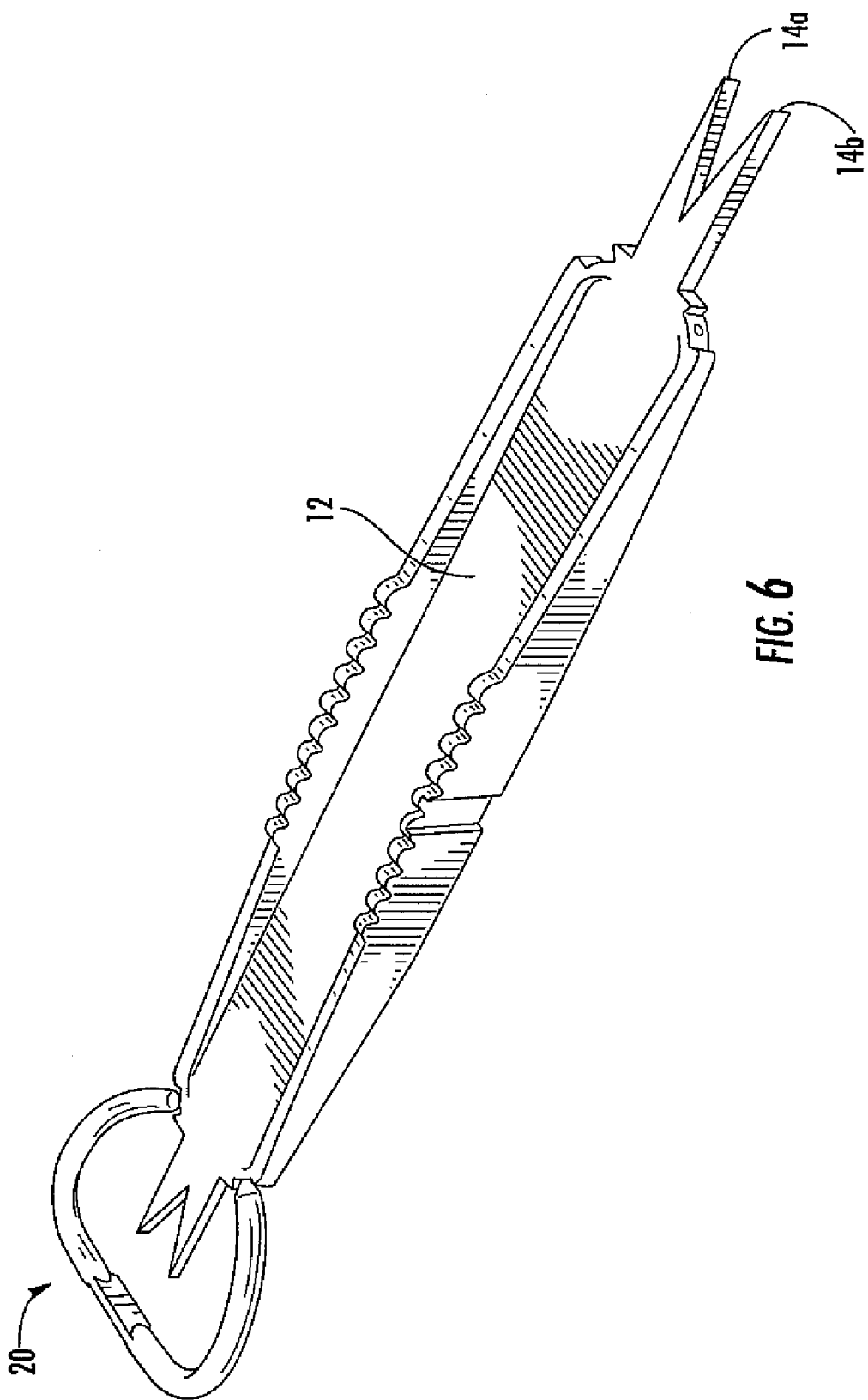
FIG. 6 shows the slceral marker with one of the protective guards removed.

With reference to FIGS. 4-6, the ends 22a and 22b of the guard 18 rigidly connect the curved strip 22 to the end 14, but a user grasping the curved strip 22 may exert force on the ends 22a and 22b by grasping the curved strip approximately at the midpoint M thereof beyond the distal ends of the points 14a and 14b and moving the strip 22 up and down or in a twisting motion so as to bend the material of the connection ends 22a and 22b repeatedly in opposite directions and break the ends 22a and 22b from the end 14 to remove the guard 18. Once the guard 18 is removed, the points 14a and 14b may be used to mark the sclera, and the marker 10 thereafter disposed. If, alternatively, use of the points 16a and 16b is desired, the guard 20 may be removed in a similar manner.

The guards 18 and 20 advantageously protect the points associated with the ends 14 and 16 so that the points are not damaged during storage, shipping, and the like. Further, it is advantageous from sterility considerations to avoid contact of the points with anything, which purpose the guards promote. The guards also advantageously avert potential disruption of the sterile packaging by preventing the points of the ends from poking through or otherwise rupturing the sterile packaging in which the marker is stored. However, when the marker is to be used, the guard of the end which is to be used may be readily and quickly removed, while the remaining guard remains in place to protect the user from the unused ends which will now lie in the user's palm. In this regard, the profile of the guards 18 and 20 is flat and aligned with the planar dimensions of the marker 10 so as to not detract from the flat profile for handling comfort. The flat profile of the guards is likewise harmonious with packaging.

The one-piece molded construction provides economy and is superior to having caps or other additional components fitted onto the ends to protect the points. As will be appreciated, such friction fitted caps and the like would involve additional and separate manufacturing, would be expensive to assemble and would also tend to fall off during shipping or handling, rendering them useless. The disclosure provides an economical and useful improvement which cleverly provides a single-use scleral marker having a configuration which protects the points, yet renders the marker easy to configure for use.

The foregoing embodiments are susceptible to considerable variation in practice. Accordingly, the embodiments are not intended to be limited to the specific exemplifications set forth hereinabove. Rather, the foregoing embodiments are within the spirit and scope of the appended claims, including the equivalents thereof available as a matter of law.

What is claimed is:

1. A single-use scleral marker, comprising: a one-piece molded-plastic marker having an elongate body; a pair of opposite forked ends, and a pair of removable guards, each of the guards encircling one of the ends and having connection ends which connect the guard to the body, wherein the connection ends may be broken by exerting a bending force thereon to enable the guard to be removed.

2. The marker of claim 1, wherein each guard comprises a curved strip positioned to lie in a common horizontal plane with the forked end.

3. A method of administering a sterile intravitreal injection using a packaged single-use scleral marker, comprising the steps of:
   providing a scleral marker comprising a one-piece molded-plastic marker having an elongate body; a pair of opposite forked ends, and a pair of removable guards, each of the guards encircling one of the ends and having connection ends which connect the guard to the body,
   breaking the connection ends of one of the guards by exerting a bending force and removing the guard from one of the forked ends to expose the forked end, and
   using the exposed forked end to mark an intravitreal injection site.

* * * * *